(12) United States Patent
Normand et al.

(10) Patent No.: US 12,279,631 B2
(45) Date of Patent: Apr. 22, 2025

(54) MARINE PROTEIN HYDROSYLATE COMPOSITIONS WITH REDUCED MALODOR

(71) Applicant: Firmenich SA, Geneva (CH)

(72) Inventors: Valery Normand, Plainsboro, NJ (US); Denis Shcherbakov, Plainsboro, NJ (US); Dattatreya Banavara, Plainsboro, NJ (US); Jian Zhang, Plainsboro, NJ (US)

(73) Assignee: Firmenich SA, Satigny (CH)

( * ) Notice: Subject to any disclaimer, the term of this patent is extended or adjusted under 35 U.S.C. 154(b) by 1427 days.

(21) Appl. No.: 16/610,742

(22) PCT Filed: May 15, 2018

(86) PCT No.: PCT/EP2018/062451
§ 371 (c)(1),
(2) Date: Nov. 4, 2019

(87) PCT Pub. No.: WO2018/210788
PCT Pub. Date: Nov. 22, 2018

(65) Prior Publication Data
US 2020/0154733 A1    May 21, 2020

Related U.S. Application Data

(60) Provisional application No. 62/507,961, filed on May 18, 2017.

(30) Foreign Application Priority Data

Oct. 24, 2017    (EP) ..................................... 17198031

(51) Int. Cl.
*A23J 3/04*       (2006.01)
*A23J 3/34*       (2006.01)
(Continued)

(52) U.S. Cl.
CPC ................. *A23J 3/04* (2013.01); *A23L 27/84* (2016.08); *A23L 33/105* (2016.08); *A23J 3/341* (2013.01); *A23V 2002/00* (2013.01)

(58) Field of Classification Search
CPC ...... A23J 3/04; A23J 3/341; A23J 3/30; A23J 3/34; A23L 27/84; A23L 33/105; A23L 33/18; A23V 2002/00; A23V 2200/00; A23V 2200/15; A23V 2200/16; A23V 2250/00; A23V 2250/02; A23V 2250/032;
(Continued)

(56) References Cited

U.S. PATENT DOCUMENTS

| 2007/0231449 A1* | 10/2007 | Cherukuri | A61Q 19/08 426/618 |
| 2013/0084358 A1* | 4/2013  | Tams      | C12C 7/28 426/12 |
| 2014/0087033 A1* | 3/2014  | McKedy    | B65D 81/2084 206/204 |

FOREIGN PATENT DOCUMENTS

| EP | 280415 A    | * | 8/1988  | ............. A23J 1/02 |
| EP | 346909 A    | * | 12/1989 | ............. A23K 30/00 |
| WO | WO-0178521 A2 | * | 10/2001 | ............. A23K 10/14 |

* cited by examiner

*Primary Examiner* — Emily M Le
*Assistant Examiner* — Tynesha L McClain
(74) *Attorney, Agent, or Firm* — Robert S. Dailey

(57) ABSTRACT

The aspects presented herein provide methods and compositions for the reduction or suppression of marine protein hydrolysate malodor by employing rice extract and/or a solid acid, preferably selected from malic acid, tartaric acid and citric acid.

14 Claims, 2 Drawing Sheets

(51) Int. Cl.
*A23L 27/00* (2016.01)
*A23L 33/105* (2016.01)

(58) Field of Classification Search
CPC ........ A23V 2250/044; A23V 2250/056; A23V 2250/55
USPC ........................................................ 426/657
See application file for complete search history.

MARINE PROTEIN HYDROSYLATE COMPOSITIONS WITH REDUCED MALODOR

CROSS REFERENCE TO RELATED APPLICATIONS

This application claims priority to U.S. Provisional Patent Application Ser. No. 62/507,961, filed May 18, 2017, and European Patent Application Serial No. 17198031.1, filed Oct. 24, 2017, the entire contents of which are hereby incorporated by reference in their entirety.

FIELD

The various aspects presented herein relate to methods and compositions for the reduction or suppression of marine protein hydrolysate malodor.

BACKGROUND

Fish has long been recognized as health-promoting food, and as a source of nutrients or ingredients with functional properties for use both in food and feed. Protein hydrolysates from fish and other marine sources have many utilities, for example in production of specialty ingredients for human consumption, in aquaculture and domestic animal feed, and as an additive in pet food.

However, protein hydrolysates from fish and other marine sources frequently possess fishy odors and rancid off odors, which may make the protein hydrolysates less desirable as ingredients for human consumption, for example. Consequently, there is a need for protein hydrolysates from fish and other marine sources where the fishy odor and/or rancid off odors are reduced or suppressed.

SUMMARY

One aspect presented herein, provides a composition, comprising:
 a. a marine protein hydrolysate; and
 b. at least one additive, selected from the group consisting of: a rice extract, and a solid acid,
  wherein the at least one additive is present in an amount effective to reduce or suppress a malodor associated with malodor compounds present in the marine protein hydrolysate.

One aspect presented herein provides a method, comprising:
 a. obtaining a marine protein hydrolysate; and
 b. mixing at least one additive, selected from the group consisting of: a rice extract, and a solid acid, with the marine protein hydrolysate,
  wherein the method reduces or suppresses malodor associated with malodor compounds, and
  wherein the at least one additive is present in an amount effective to reduce or suppress a malodor associated with malodor compounds present in the marine protein hydrolysate.

In one aspect, the at least one additive is present in an amount effective to reduce or suppress a taste associated with malodor compounds present in the marine protein hydrolysate.

In one aspect, the malodor compounds comprise di-methyl amines, tri-methyl amines, lipid oxidation products, and any combination thereof.

In one aspect, the rice extract comprises from 14 to 18% by weight protein, from 16 to 25% by weight fat, and from 9 to 51% by weight carbohydrate.

In one aspect, the solid acid is an amorphous crystalline solid at temperatures below 40 degrees Celsius.

In one aspect, the solid acid is an organic acid.

In one aspect, the solid acid is selected from the group consisting of: malic acid, tartaric acid and citric acid. In some aspects, the solid acid is citric acid.

In one aspect, the solid acid comprises granules.

In one aspect, the effective amount of the rice extract is from 1 to 5% by weight of the composition.

In one aspect, the effective amount of the rice extract is from 1 to 2% by weight of the composition.

In one aspect, the effective amount of the rice extract is 2% by weight of the composition.

In one aspect, the effective amount of the rice extract is 1% by weight of the composition.

In one aspect, the effective amount of the solid acid is from 1 to 5% by weight of the composition.

In one aspect, the effective amount of the solid acid is from 1 to 2% by weight of the composition.

In one aspect, the effective amount of the solid acid is 2% by weight of the composition.

In one aspect, the effective amount of the solid acid is 1% by weight of the composition.

In one aspect, the solid acid is selected from the group consisting of: malic acid, tartaric acid and citric acid.

In one aspect, the composition comprises a marine protein hydrolysate, rice extract at an amount from 1 to 5% by weight of the composition, and citric acid at an amount from 1 to 5% by weight of the composition.

In one aspect, the citric acid comprises granules.

DETAILED DESCRIPTION

Figure 1:
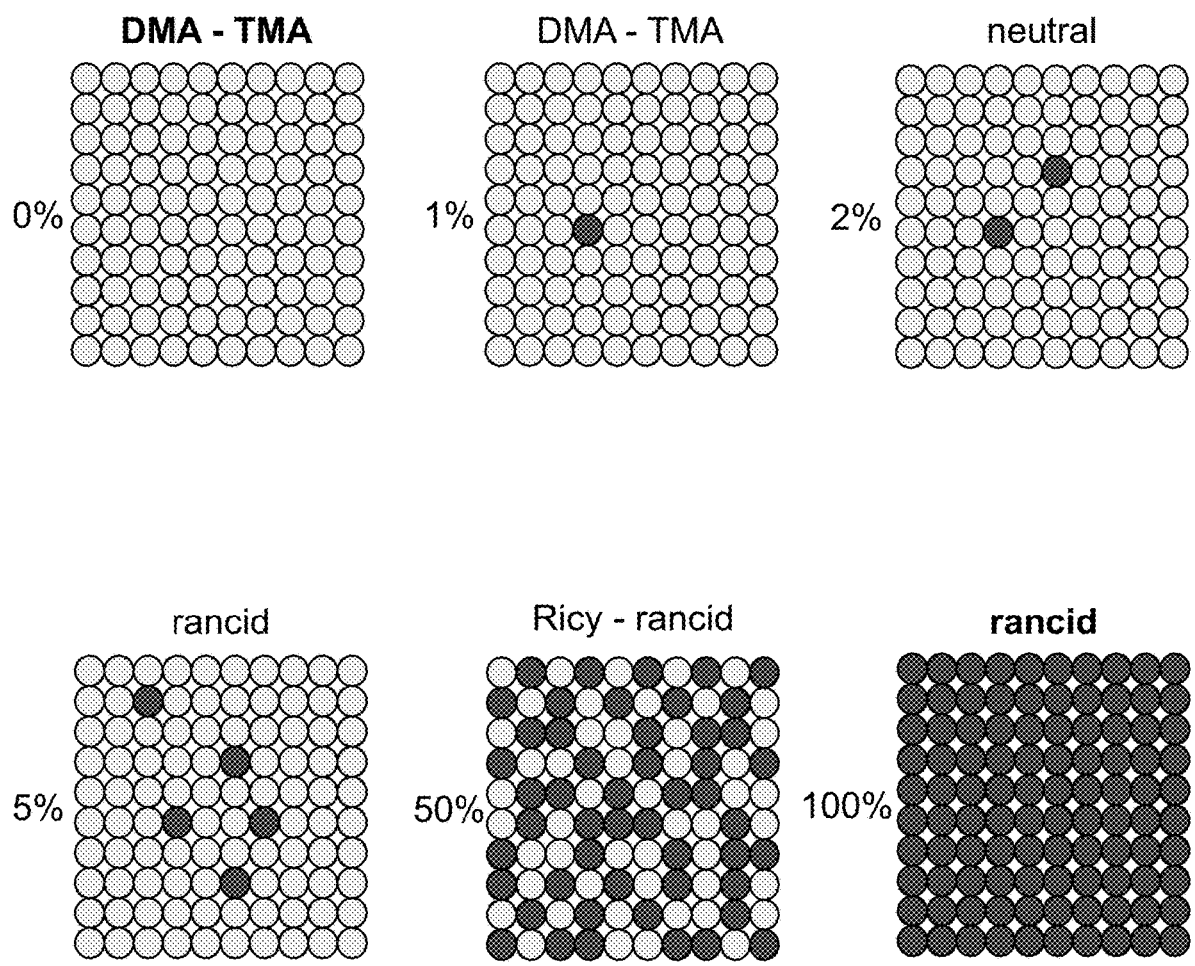
FIG. 1 shows the results of the headspace analysis of compositions according to some embodiments of the present invention comprising a marine protein hydrolysate, and rice extract.

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

The various aspects presented herein relate to methods and compositions for the reduction or suppression of marine protein hydrolysate malodor.

Accordingly, some aspects provide a composition, comprising:
   a. a marine protein hydrolysate; and
   b. at least one additive, selected from the group consisting of: a rice extract, and a solid acid,
      wherein the at least one additive is present in an amount effective to reduce or suppress a malodor associated with malodor compounds present in the marine protein hydrolysate.

In one aspect, the malodor compounds comprise di-methyl amines, tri-methyl amines, lipid oxidation products, and any combination thereof.

One aspect presented herein provides a method, comprising:
   a. obtaining a marine protein hydrolysate; and
   b. mixing at least one additive, selected from the group consisting of: a rice extract, and a solid acid, with the marine protein hydrolysate,
      wherein the method reduces or suppresses malodor associated with malodor compounds, and
      wherein the at least one additive is present in an amount effective to reduce or suppress a malodor associated with malodor compounds present in the marine protein hydrolysate.

In some aspects, the marine protein hydrolysate and the at least one additive are dry powders, and the dry powders are blended together to obtain a composition according to some aspects presented herein.

In some aspects, the amount of the marine protein hydrolysate in the composition is from 95% to 99% by weight of the composition. Alternatively, in some aspects, the amount of the marine protein hydrolysate in the composition is from 96% to 99% by weight of the composition. Alternatively, in some aspects, the amount of the marine protein hydrolysate in the composition is from 97% to 99% by weight of the composition. Alternatively, in some aspects, the amount of the marine protein hydrolysate in the composition is from 98% to 99% by weight of the composition.

Alternatively, in some aspects, the amount of the marine protein hydrolysate in the composition is from 95% to 98% by weight of the composition. Alternatively, in some aspects, the amount of the marine protein hydrolysate in the composition is from 95% to 97% by weight of the composition. Alternatively, in some aspects, the amount of the marine protein hydrolysate in the composition is from 95% to 96% by weight of the composition.

In some aspects, the amount of the marine protein hydrolysate in the composition is 95, or 96, or 97, or 98, or 99% by weight of the composition.

In some aspects, the solid acid comprises pulverized particles. In alternative aspects, the solid acid comprises granules.

Without intending to be limited to any particular theory, in some aspects, the undesirable olfactive properties of the marine protein hydrolysate are due, at least in part, by the presence of di- and tri-methyl amines, and other oxidation products in the marine protein hydrolysate, wherein the di- and tri-methyl amines, and other oxidation products are present in the marine protein hydrolysate in an amount above their respective odor detection thresholds. Examples of other oxidation products include, but are not limited to, lipid oxidation products.

In some aspects, the addition of the at least one additive to the marine protein hydrolysate reduces or suppresses the malodor associated with the presence of di- and tri-methyl amines, and other oxidation products, including lipid oxidation products (collectively, malodor compounds) in the marine protein hydrolysate by: (i) the rice extract absorbing the malodor compounds; and/or (ii) the solid acid rendering the malodor compounds odorless via protonation.

In some aspects, the effective amount of the at least one additive masks the taste imparted by the malodor compounds. In some aspects, the masking is partial.

In some aspects, the at least one additive is present in an amount effective to reduce or suppress a malodor associated with malodor compounds present in the marine protein hydrolysate. In further aspects, the at least one additive is present in an amount that does not adversely affect the olfactive properties, and/or the taste of the marine protein hydrolysate. For example, by way of illustration, the rice extract may impart a rancid odor to the marine protein hydrolysate, if present above a certain amount. In another example, the rice extract may impart a rice odor to the marine protein hydrolysate, if present above a certain amount. In another example, where the solid acid comprises citric acid, the citric acid may impart a citrus odor to the marine protein hydrolysate, if present above a certain amount. In another example, where the solid acid comprises citric acid, the citric acid may impart an acid odor to the marine protein hydrolysate, if present above a certain amount.

In some aspects, the ability of the rice extract and/or the solid acid to reduce or suppress the malodor and/or mask the taste associated with the malodor compounds is influenced by the physical properties of the rice extract and/or the solid acid. Physical properties include, but are not limited to particle size, pore volume, surface area, average pore diameter, pore-size distribution and the like.

In some aspects, the rate of protonation of the malodor compounds by the solid acid is influenced by the surface area of the solid acid. In some aspects, the greater the surface area of the solid acid, the greater the rate of protonation of the malodor compounds. In some aspects, the effective amount of the solid acid is lower, if the rate of protonation is high.

In some aspects, the effective amount of the rice extract is from 1 to 5% by weight of the composition. Alternatively, in some aspects, the effective amount of the rice extract is from 2 to 5% by weight of the composition. Alternatively, in some aspects, the effective amount of the rice extract is from 3 to 5% by weight of the composition. Alternatively, in some aspects, the effective amount of the rice extract is from 4 to 5% by weight of the composition.

Alternatively, in some aspects, the effective amount of the rice extract is from 1 to 4% by weight of the composition. Alternatively, in some aspects, the effective amount of the rice extract is from 1 to 3% by weight of the composition. Alternatively, in some aspects, the effective amount of the rice extract is from 1 to 2% by weight of the composition.

In some aspects, the effective amount of the rice extract is from 1 to 2% by weight of the composition.

In some aspects, the effective amount of the rice extract is 1, or 2, or 3, or 4, or 5% by weight of the composition.

In some aspects, the effective amount of the rice extract is 2% by weight of the composition.

In some aspects, the effective amount of the rice extract is 1% by weight of the composition.

In some aspects, the effective amount of the solid acid is from 1 to 5% by weight of the composition. Alternatively, in some aspects, the effective amount of the solid acid is from 2 to 5% by weight of the composition. Alternatively, in some aspects, the effective amount of the solid acid is from 3 to 5% by weight of the composition. Alternatively, in some aspects, the effective amount of the solid acid is from 4 to 5% by weight of the composition.

Alternatively, in some aspects, the effective amount of the solid acid is from 1 to 4% by weight of the composition. Alternatively, in some aspects, the effective amount of the solid acid is from 1 to 3% by weight of the composition. Alternatively, in some aspects, the effective amount of the solid acid is from 1 to 2% by weight of the composition.

In some aspects, the effective amount of the solid acid is 1, or 2, or 3, or 4, or 5% by weight of the composition.

In some aspects, the effective amount of the solid acid is from 1 to 2% by weight of the composition.

In some aspects, the effective amount of the solid acid is 2% by weight of the composition.

In some aspects, the effective amount of the solid acid is 1% by weight of the composition.

In some aspects, the solid acid is an amorphous crystalline solid at temperatures below 40 degrees Celsius. In some aspects, the solid acid is an organic acid. In some aspects, the solid acid is a food-grade acidic powder. In some aspects, the solid acid is selected from the group consisting of: malic acid, tartaric acid and citric acid. In some aspects, the solid acid is citric acid.

In some aspects, the composition comprises a marine protein hydrolysate, rice extract at an amount from 1 to 5% by weight of the composition, and citric acid at an amount from 1 to 5% by weight of the composition.

In some aspects, the citric acid comprises granules. In alternate aspects, the citric acid comprises pulverized particles.

In some aspects, the rice extract comprises from 14 to 18% by weight protein, from 16 to 25% by weight fat, and from 9 to 51% by weight carbohydrate. In some aspects, the rice extract is the rice extract sold under the trade name NU-RICE®. In some aspects, the rice extract may be gluten-free.

The Marine Protein Hydrolysate:

As used herein, the term "marine protein hydrolysate" refers to a protein hydrolysate obtained from an enzymatic digestion of material obtained from marine animals, such as, for example, fish, mollusks, crustaceans, marine algae, and the like.

In some aspects, the marine protein hydrolysate is a fish protein hydrolysate. Fish suitable for material from which to obtain a fish protein hydrolysate suitable for use according to some aspects presented herein include salmon, cod, Tilapia, clams, oysters, and the like. Fish protein hydrolysates suitable for use according to some aspects presented herein may be obtained by any method selected by one of ordinary skill in the art.

One example of a method to obtain a fish protein hydrolysate suitable for use according to some aspects presented herein is disclosed in International Patent Application Publication No. WO 2005002605 A1.

Another example of a method to obtain a fish protein hydrolysate suitable for use according to some aspects presented herein is disclosed in U.S. Pat. No. 3,857,966 A.

Another example of a method to obtain a fish protein hydrolysate suitable for use according to some aspects presented herein is disclosed in Kristinsson G., et al. (2000), Critical Reviews in Food Science and Nutrition, 40:1, pg 43-81.

Another example of a method to obtain a fish protein hydrolysate suitable for use according to some aspects presented herein is disclosed in Kristinsson G and Rasco, B. (2000), J. Agric. Food Chem., 48, pg 657-666.

Another example of a method to obtain a fish protein hydrolysate suitable for use according to some aspects presented herein is disclosed in He, S., et al. (2015), J. Food Science, 80:1, pg E108-E115.

Another example of a method to obtain a fish protein hydrolysate suitable for use according to some aspects presented herein is disclosed in Norwegian Patent No. 20040450.

The process for making fish protein hydrolysate typically begins with fresh or fresh frozen fish muscle tissue which is minced and mixed with water at a ratio 1:1 in an incubator (e.g., but not limited to a 1-20 $m^3$ volume incubator). The temperature is raised to 50-55° C. while the mixture stirred from 50-80 rpm. An enzyme cocktail consisting of a mixture of proteases and peptidases is added (e.g., Protamex® from NOVOZYMES, Denmark) to the mixture and the temperature is brought to about 50 to 55° C. and the homogenate formed is incubated for 45 min at 50-55° C. at pH 6-8, alternatively at pH 6-7. Then the temperature is raised to 85-90° C. and kept at that temperature for about 10-15 min to inactivate the enzymes. The incubate is passed through a sieve to remove bones and debris, then the soluble fraction is separated from the indigestible/insoluble material using centrifugation after which the peptide rich soluble fraction is dehydrated into a concentrate, which is used for spray-drying into a powder.

In some aspects, the fish protein hydrolysate is obtained according to a method comprising the steps of:

a. mixing marine raw materials with water an and enzyme to form a marine material mixture; wherein the enzyme is an endopeptidase, and wherein the marine raw materials comprise fish;
 b. homogenizing the marine material mixture to form a homogenate;
 c. heating the homogenate for a time period of up to about 45 minutes to form an incubate;
 d. deactivating the enzyme to form an incubate with a deactivated enzyme;
 e. optionally separating the bones from the incubate to form an incubate having a water soluble protein rich fraction;
 f. separating the water soluble and peptide rich fraction from the incubate to obtain a hydrolsysate peptide product;
 g. optionally filtering or ultrafiltering the hydrolsysate to remove micro-particles; and
 h. optionally spray drying the hydrolysate to form a free-flowing powder.

In some aspects, the fish protein hydrolysate is derived from cod. In some aspects, the fish protein hydrolysate described in Norwegian Patent No. 20040450.

Products Comprising Compositions According to Some Aspects Presented Herein: Compositions according to some aspects presented herein may be incorporated into a number of food products. Examples of food products include, but are not limited to, powdered beverages, sports nutrition products, cereal bars, and the like.

One example of a food product suitable for a composition according to some aspects presented herein is the pharmaceutical or nutritional preparation disclosed in International Patent Application Publication No. WO 2005002605 A1.

Another example of a food product suitable for a composition according to some aspects presented herein is the preparation disclosed in U.S. Patent Application Publication No. 2003/009972 A1.

Another example of a food product suitable for a composition according to some aspects presented herein is the preparation disclosed in U.S. Patent Application Publication No. 2007/0166411 A1.

The present invention is best illustrated but is not limited to the following examples.

EXAMPLES

Example 1: Head Space Analysis of Compositions According to Some Aspects Presented Herein The following compositions were generated by mixing dry powders of the individual constituents, according to the combinations set forth in the table below.

| Marine Protein Hydrolysate Powder (% w/w of composition) | Nu-Rice Powder (% w/w of composition) | Citric Acid Powder (% w/w of composition) |
|---|---|---|
| 100 | 0 | 0 |
| 99 | 1 | 0 |
| 98 | 2 | 0 |
| 95 | 5 | 0 |
| 50 | 50 | 0 |
| 0 | 100 | 0 |

Eight grams of the compositions were placed into a separate 10×10 array of individual 15 cm tall containers and sealed. After a sufficient period of time, the odor of the headspace of each container was analyzed by six to ten volunteer testers, for the presence of DMA/TMA, rice odor and/or rancid odors. According to the design of the experiment, a neutral odor was deemed to be optimal. The results are shown in FIG. 1, wherein compositions comprising marine protein hydrolysate and from 2 to 5% rice extract had head space with a neutral odor. Compositions comprising greater than 5% rice extract were found to have a rice, or rancid odor to the headspace.

Example 2: Head Space Analysis of Compositions According to Some Aspects Presented Herein The following compositions were generated by mixing dry powders of the individual constituents, according to the combinations set forth in the table below.

| Marine Protein Hydrolysate Powder (% w/w of composition) | Nu-Rice Powder (% w/w of composition) | Citric Acid Powder (% w/w of composition) |
|---|---|---|
| 100 | 0 | 0 |
| 99 | 0 | 1 |
| 98 | 0 | 2 |
| 95 | 0 | 5 |
| 90 | 0 | 10 |
| 0 | 0 | 100 |

Figure 2:
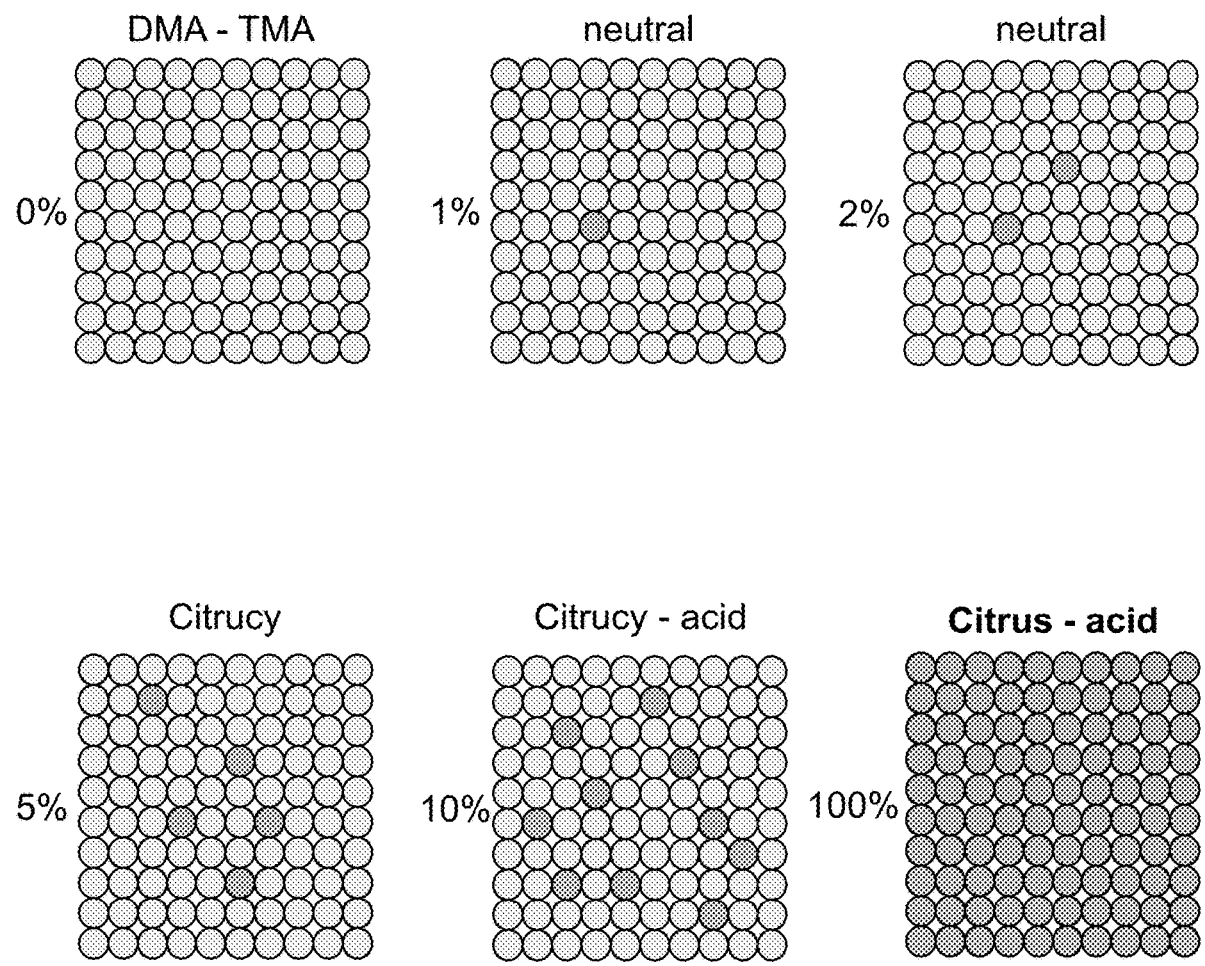
FIG. 2 shows the results of the headspace analysis of compositions according to some embodiments of the present invention comprising a marine protein hydrolysate, and citric acid granules.

Eight grams of the compositions were placed into a separate 10×10 array of individual 15 cm tall containers and sealed. After a sufficient period of time, the odor of the headspace of each container was analyzed by six to ten volunteer testers, for the presence of DMA/TMA, citrus odor and/or acid odors. According to the design of the experiment, a neutral odor was deemed to be optimal. The results are shown in FIG. 2, wherein compositions comprising marine protein hydrolysate and from 1 to 2% citric acid had head space with a neutral odor. Compositions comprising greater than 2% citric acid were found to have a citrus, or acid odor to the headspace.

Example 3: Head Space Analysis of Compositions According to Some Aspects Presented Herein The following compositions were generated by mixing dry powders of the individual constituents, according to the combinations set forth in the table below.

| Marine Protein Hydrolysate Powder (% w/w of composition) | Nu-Rice Powder (% w/w of composition) | Citric Acid Powder (% w/w of composition) | Fish Malodor Detected (0-5 scale) |
|---|---|---|---|
| 100 | 0 | 0 | 4.08 ± 1.11 |
| 98 | 2 | 0 | 3.00 ± 1.55 |
| 96 | 2 | 2 (pulverized) | 2.17 ± 1.47 |
| 96 | 2 | 2 (granular) | 2.33 ± 1.37 |
| 99 | 1 | 0 | 2.29 ± 1.11 |
| 98 | 1 | 1 (pulverized) | 2.00 ± 0.82 |
| 97 | 1 | 2 (pulverized) | 1.79 ± 0.99 |

Eight grams of the compositions were placed into a separate 10×10 array of individual 15 cm tall containers and sealed. After a sufficient period of time, the odor of the headspace of each container was analyzed by six to ten volunteer testers, for the presence of fish odors, and asked to rank the fish odor from 0 to 5, where 0 was no detectable fish odor, and 5 was an intense fish odor. The composition where the fish odor was most effectively reduced comprised 97% marine protein hydrolysate, 1% rice extract, and 2% citric acid powder.

In a separate experiment, the ability of a corn husk particle sold under the trade name DEODAZORB® to reduce fish odor was tested. A composition comprising 50% w/w marine protein hydrolysate and 50% w/w DEODAZORB® was tested according to the methods described above. A separate control composition comprising 50% w/w marine protein hydrolysate and 50% w/w rice extract was also evaluated as a control. Evaluation by a 5-6 member panel concluded that the composition comprising 50% w/w marine protein hydrolysate and 50% w/w DEODAZORB® had no effect on MPH malodor, while the control composition reduced MPH malodor.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A marine protein hydrosylate composition, the composition comprising:
    (a) a marine protein hydrolysate;
    (b) one or more malodor compounds, wherein the one or more malodor compounds comprise trimethylamine, dimethylamines, lipid oxidation products, or any combinations thereof; and
    (c) one or more malodor-reducing additives, wherein the one or more malodor-reducing additives comprise a rice extract, a solid acid, or a combination thereof.

2. The marine protein hydrosylate composition of claim 1, wherein the one or more malodor-reducing additives comprise rice extract, and wherein the rice extract comprises from 14 to 18% by weight protein, from 16 to 25% by weight fat, and from 9 to 51% by weight carbohydrate.

3. The marine protein hydrosylate composition of claim 1, wherein the one or more malodor-reducing additives comprise a solid acid, and wherein the solid acid comprises granules.

4. The marine protein hydrosylate composition of claim 2, wherein the rice extract is present in the marine protein hydrosylate composition at a concentration ranging from 1 to 5% by weight of the marine protein hydrosylate composition.

5. The marine protein hydrosylate composition of claim 3, wherein the solid acid is present in the marine hydrosylate composition at a concentration ranging from 1 to 5% by weight of the marine protein hydrosylate composition.

6. The marine protein hydrosylate composition of claim 3, wherein the solid acid is selected from the group consisting of: malic acid, tartaric acid, and citric acid.

7. The marine protein hydrosylate composition of claim 1, wherein the marine protein hydrosylate composition comprises rice extract at a concentration ranging from 1 to 5% by weight of the marine protein hydrosylate composition, and comprises citric acid at a concentration ranging from 1 to 5% by weight of the composition.

8. A method of reducing malodor of a marine protein hydrosylate, the method comprising:
(a) providing a marine protein hydrolysate composition, which comprises a marine protein hydrosylate and one or more malodor compounds, wherein the one or more malodor compounds comprise trimethylamine, dimethylamines, lipid oxidation products, or any combinations thereof; and
(b) mixing one or more malodor-reducing additives with the marine hydrolysate composition, wherein the one or more malodor-reducing additives comprise a rice extract, a solid acid, or a combination thereof.

9. The method of claim 8, wherein the one or more malodor-reducing additives comprise rice extract, and wherein the rice extract comprises from 14 to 18% by weight protein, from 16 to 25% by weight fat, and from 9 to 51% by weight carbohydrate.

10. The method of claim 8, wherein the one or more malodor-reducing additives comprise a solid acid, and wherein the solid acid comprises granules.

11. The method of claim 9, wherein the rice extract is mixed with the marine protein hydrosylate composition at a concentration ranging from 1 to 5% by weight of the marine protein hydrosylate composition.

12. The method of claim 10, wherein the solid acid is mixed with the marine protein hydrosylate composition at a concentration ranging from 1 to 5% by weight of the marine protein hydrosylate composition.

13. The method of claim 12, wherein the solid acid is selected from the group consisting of: malic acid, tartaric acid, and citric acid.

14. The method of claim 8, wherein the rice extract is mixed with the marine protein hydrosylate composition at a concentration ranging from 1 to 5% by weight of the marine protein hydrosylate composition, and wherein citric acid is mixed with the marine protein hydrosylate composition at a concentration ranging from 1 to 5% by weight of the composition.

\* \* \* \* \*